(12) United States Patent
Ebata

(10) Patent No.: US 11,116,475 B2
(45) Date of Patent: Sep. 14, 2021

(54) ULTRASOUND DIAGNOSTIC APPARATUS AND METHOD FOR CONTROLLING ULTRASOUND DIAGNOSTIC APPARATUS

(71) Applicant: FUJIFILM Corporation, Tokyo (JP)

(72) Inventor: Tetsurou Ebata, Ashigara-kami-gun (JP)

(73) Assignee: FUJTFIT.M Corporation, Tokyo (JP)

( * ) Notice: Subject to any disclaimer, the term of this patent is extended or adjusted under 35 U.S.C. 154(b) by 695 days.

(21) Appl. No.: 15/883,784

(22) Filed: Jan. 30, 2018

(65) Prior Publication Data

US 2018/0168546 A1 Jun. 21, 2018

Related U.S. Application Data

(63) Continuation of application No. PCT/JP2016/063992, filed on May 11, 2016.

(30) Foreign Application Priority Data

Aug. 31, 2015 (JP) .............................. JP2015-170449

(51) Int. Cl.
*A61B 8/00* (2006.01)
*A61B 8/14* (2006.01)
*A61B 8/08* (2006.01)

(52) U.S. Cl.
CPC .............. *A61B 8/4245* (2013.01); *A61B 8/14* (2013.01); *A61B 8/5207* (2013.01); *A61B 8/54* (2013.01)

(58) Field of Classification Search
None
See application file for complete search history.

(56) References Cited

U.S. PATENT DOCUMENTS

2007/0112266 A1\* 5/2007 Kishimoto ............. A61B 8/546
600/437
2009/0226062 A1\* 9/2009 Nakamura .............. G06F 16/51
382/128
(Continued)

FOREIGN PATENT DOCUMENTS

JP 4-224738 A 8/1992
JP 10-201760 A 8/1998
(Continued)

OTHER PUBLICATIONS

International Preliminary Report on Patentability and Written Opinion of the International Searching Authority (Forms PCT/IB/326, PCT/IB/373 and PCT/ISA/237) for Application No. PCT/JP2016/063992, dated Mar. 15, 2018, with an English translation.
(Continued)

*Primary Examiner* — Joel F Brutus
(74) *Attorney, Agent, or Firm* — Birch, Stewart, Kolasch & Birch, LLP

(57) ABSTRACT

An ultrasound diagnostic apparatus includes: an ultrasound probe; an imaging unit that transmits and receives an ultrasound beam to and from a subject using the ultrasound probe and converts a received signal output from the ultrasound probe into an image to generate an ultrasound image of the subject for each frame; a part determination unit that determines an imaging part of the subject using the ultrasound image generated by the imaging unit; a probe state determination unit that determines whether the ultrasound probe is in an aerial emission state or a contact state with the subject; and an apparatus control unit that controls the part determination unit such that part determination is not performed in a case in which the probe state determination unit determines that the ultrasound probe is in the aerial emission state and the part determination is performed in a case in which the probe state determination unit determines that the (Continued)

ultrasound probe has been changed from the aerial emission state to the contact state with the subject.

12 Claims, 6 Drawing Sheets

(56) References Cited

U.S. PATENT DOCUMENTS

2014/0037168 A1   2/2014  Iskikawa et al.
2015/0133786 A1*  5/2015  Wong .................. A61B 8/4427
                                                                600/441

FOREIGN PATENT DOCUMENTS

| JP | 2006-20667 A | 1/2006 |
| JP | 2012-90662 A | 5/2012 |
| JP | 2012-217769 A | 11/2012 |

OTHER PUBLICATIONS

International Search Report and English translation (Form PCT/ISA/210) for Application No. PCT/JP2016/063992, dated Jul. 26, 2016.

\* cited by examiner

ULTRASOUND DIAGNOSTIC APPARATUS AND METHOD FOR CONTROLLING ULTRASOUND DIAGNOSTIC APPARATUS

CROSS-REFERENCE TO RELATED APPLICATIONS

This application is a Continuation of PCT International Application No. PCT/JP2016/063992 filed on May 11, 2016, which claims priority under 35 U.S.C. § 119(a) to Japanese Patent Application No. 2015-170449 filed on Aug. 31, 2015. The above application is hereby expressly incorporated by reference, in its entirety, into the present application.

BACKGROUND OF THE INVENTION

1. Field of the Invention

The present invention relates to an ultrasound diagnostic apparatus and a method for controlling the ultrasound diagnostic apparatus, and more particularly, to an ultrasound diagnostic apparatus that determines an imaging part of a subject on the basis of an ultrasound image.

2. Description of the Related Art

In the related art, an ultrasound diagnostic apparatus using an ultrasound image has been put to practical use in the medical field. In general, in this type of ultrasound diagnostic apparatus, an ultrasound probe provided with an array transducer scans a subject with an ultrasound beam and receives ultrasound echoes from the subject and the received signal is electrically processed to generate an ultrasound image.

In a case in which the ultrasound diagnostic apparatus is used to diagnose a plurality of imaging parts of the subject, appropriate imaging conditions vary depending on imaging parts in order to obtain ultrasound images suitable for diagnosis for each imaging part. Therefore, for example, JP1992-224738A (JP-H04-224738A) discloses an ultrasound diagnostic apparatus which automatically determines an imaging part from a generated ultrasound image, using a pattern matching process, and sets a scanning parameter most suitable for the imaging part on the basis of the determination result.

SUMMARY OF THE INVENTION

However, in a case in which the automatic determination process is performed for each frame, the amount of calculation is increased by the automatic determination process. The increase in the amount of calculation is likely to cause, for example, a reduction in frame rate. In a case in which the image is a motion picture and the frame rate is reduced, a motion is not smooth, which is likely to hinder diagnosis. In addition, for example, the increase in the amount of calculation causes an increase in power consumption.

The invention has been made in order to solve the problems of the related art and an object of the invention is to provide an ultrasound diagnostic apparatus and a method for controlling the ultrasound diagnostic apparatus that can prevent an increase in the amount of calculation while performing part determination.

An ultrasound diagnostic apparatus according to the invention includes: an ultrasound probe; an imaging unit that transmits and receives an ultrasound beam to and from a subject using the ultrasound probe and converts a received signal output from the ultrasound probe into an image to generate an ultrasound image of the subject for each frame; a part determination unit that determines an imaging part of the subject using the ultrasound image generated by the imaging unit; a probe state determination unit that determines whether the ultrasound probe is in an aerial emission state or a contact state with the subject; and an apparatus control unit that controls the part determination unit such that part determination is not performed in a case in which the probe state determination unit determines that the ultrasound probe is in the aerial emission state and the part determination is performed in a case in which the probe state determination unit determines that the ultrasound probe has been changed from the aerial emission state to the contact state with the subject.

Preferably, the probe state determination unit detects whether a structure is present or absent in an image on the basis of a brightness distribution of the ultrasound image. Preferably, in a case in which no structure is detected in the image, the probe state determination unit determines that the ultrasound probe is in the aerial emission state. Preferably, in a case in which a structure is detected in the image, the probe state determination unit determines that the ultrasound probe is in the contact state with the subject.

Preferably, the probe state determination unit further detects an amount of movement of an observation point set in the ultrasound image between frames. Preferably, in a case in which a state in which no structure is detected in the image changes to a state in which a structure is detected in the image and the amount of movement of the observation point is equal to or less than a set value, the probe state determination unit determines that the ultrasound probe has been changed from the aerial emission state to the contact state with the subject. Preferably, in a case in which the state in which a structure is detected in the image changes to the state in which no structure is detected in the image and the amount of movement of the observation point is equal to or less than the set value, the probe state determination unit determines that the ultrasound probe has been changed from the contact state with the subject to the aerial emission state.

Preferably, after it is recognized that the part determination has been completed, the apparatus control unit controls the part determination unit such that the part determination is not performed until the ultrasound probe is determined to be changed from the aerial emission state to the contact state with the subject.

Preferably, the part determination unit calculates similarity between the ultrasound image and each imaging part and outputs a determination result on the basis of the similarity and the apparatus control unit recognizes that the part determination has been completed in a case in which the determination result is output from the part determination unit.

According to the invention, there is provided a method for controlling an ultrasound diagnostic apparatus. The method includes: a step of transmitting and receiving an ultrasound beam to and from a subject using an ultrasound probe and converting a received signal output from the ultrasound probe into an image to generate an ultrasound image of the subject for each frame; a step of determining whether the ultrasound probe is in an aerial emission state or a contact state with the subject; and a step of not determining an imaging part of the subject on the basis of the ultrasound image in a case in which it is determined that the ultrasound probe is in the aerial emission state and of determining the imaging part of the subject on the basis of the ultrasound image in a case in which it is determined that the ultrasound probe has been changed from the aerial emission state to the contact state with the subject.

According to the invention, an imaging part of the subject is not determined on the basis of the ultrasound image in a case in which it is determined that the ultrasound probe is in the aerial emission state. The part determination unit performs part determination in a case in which it is determined that the ultrasound probe has been changed from the aerial emission state to the contact state with the subject. Therefore, it is possible to prevent an increase in the amount of calculation while performing part determination.

DESCRIPTION OF THE PREFERRED EMBODIMENTS

Hereinafter, embodiments of the invention will be described with reference to the accompanying drawings.

Embodiment 1

Figure 1:
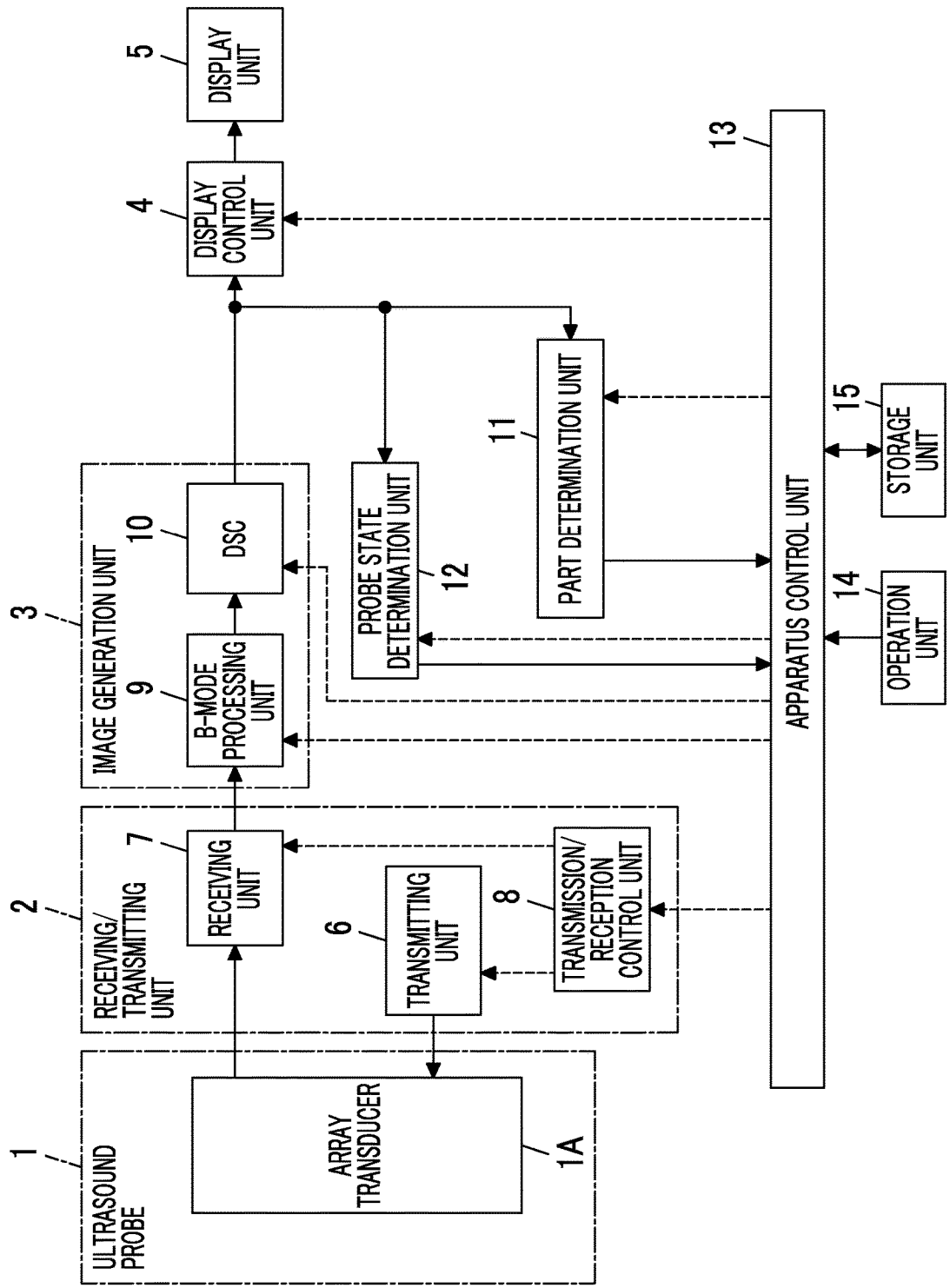
FIG. 1 is a block diagram illustrating the configuration of an ultrasound diagnostic apparatus according to Embodiment 1 of the invention.

FIG. 1 illustrates the configuration of an ultrasound diagnostic apparatus according to Embodiment 1 of the invention. The ultrasound diagnostic apparatus includes an ultrasound probe 1 provided with an array transducer 1A. An image generation unit 3 is connected to the ultrasound probe 1 through a transmitting/receiving unit 2 and a display unit 5 is connected to the image generation unit 3 through a display control unit 4.

The transmitting/receiving unit 2 includes a transmitting unit 6 and a receiving unit 7 that are connected to the array transducer 1A of the ultrasound probe 1 and a transmission/reception control unit 8 that is connected to the transmitting unit 6 and the receiving unit 7. The image generation unit 3 includes a B-mode processing unit 9 that is connected to the receiving unit 7 of the transmitting/receiving unit 2 and a digital scan converter (DSC) 10 that is connected to the B-mode processing unit 9. The display control unit 4 is connected to the DSC 10.

In addition, a part determination unit 11 and a probe state determination unit 12 are connected to the DSC 10 of the image generation unit 3.

An apparatus control unit 13 is connected to the transmission/reception control unit 8 of the transmitting/receiving unit 2, the B-mode processing unit 9 and the DSC 10 of the image generation unit 3, the display control unit 4, the part determination unit 11, and the probe state determination unit 12. In addition, an operation unit 14 and a storage unit 15 are connected to the apparatus control unit 13.

The array transducer 1A of the ultrasound probe 1 includes a plurality of ultrasound transducers that are one-dimensionally or two-dimensionally arranged. Each of the ultrasound transducers transmits ultrasonic waves in response to a driving signal supplied from the transmitting unit 6. In addition, each of the ultrasound transducers receives ultrasound echoes from a subject and outputs a received signal. Each ultrasound transducer is, for example, a transducer in which electrodes are formed on both sides of a piezoelectric body made of piezoelectric ceramic typified by lead zirconate titanate (PZT), a polymer piezoelectric element typified by polyvinylidene difluoride (PVDF), or piezoelectric single crystal typified by lead magnesium niobate-lead titanate (PMN-PT).

In a case in which a pulsed voltage or a continuous-wave voltage is applied to the electrodes of the transducer, the piezoelectric body is expanded and contracted and pulsed or continuous ultrasonic waves are generated from each transducer. The ultrasonic waves are combined to form an ultrasound beam. In addition, each transducer receives propagated ultrasonic waves, is expanded and contracted, and generates an electric signal. The electric signal is output as a received ultrasound signal.

The transmitting/receiving unit 2 transmits and receives an ultrasound beam and the image generation unit 3 generates a B-mode image signal. Therefore, the transmitting/receiving unit 2 and the image generation unit 3 form an imaging unit.

The transmitting unit 6 of the transmitting/receiving unit 2 includes, for example, a plurality of pulse generators, adjusts the amount of delay of each driving signal such that the ultrasonic waves transmitted from a plurality of ultrasound transducers in the array transducer 1A form an ultrasound beam, on the basis of a transmission delay pattern selected according to a control signal from the transmission/reception control unit 8, and supplies the driving signals to the plurality of ultrasound transducers.

Figure 2:
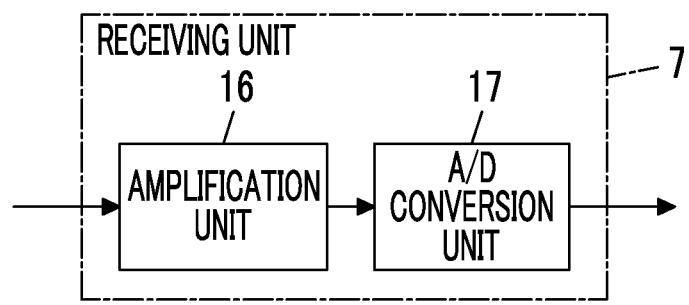
FIG. 2 is a block diagram illustrating the internal configuration of a receiving unit.

As illustrated in FIG. 2, the receiving unit 7 has a configuration in which an amplification unit 16 and an analog/digital (A/D) conversion unit 17 are sequentially connected in series. The receiving unit 7 amplifies the received signals transmitted from each ultrasound transducer of the array transducer 1A with the amplification unit 16 and performs A/D conversion for the received signals with the A/D conversion unit 17 to generate digital received data.

The transmission/reception control unit 8 controls the transmitting unit 6 and the receiving unit 7 on the basis of various control signals transmitted from the apparatus control unit 13 such that the transmission of an ultrasound pulse to a subject and the reception of an ultrasound echo from the subject are repeated at a pulse repetition frequency (PRF) interval.

Figure 3:
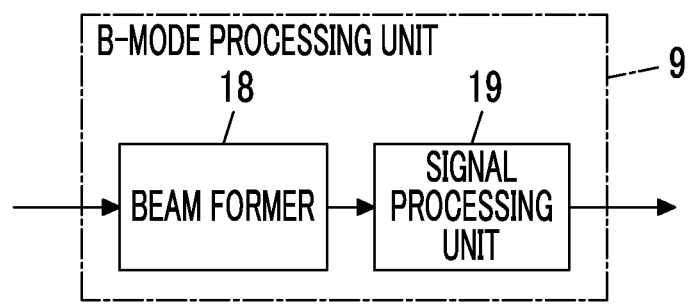
FIG. 3 is a block diagram illustrating the internal configuration of a B-mode processing unit.

The B-mode processing unit 9 of the image generation unit 3 has a configuration in which a beam former 18 and a signal processing unit 19 are sequentially connected in series, as illustrated in FIG. 3. The beam former 18 applies a delay to each received data item output from the receiving unit 7 of the transmitting/receiving unit 2 according to a sound speed or a sound speed distribution set on the basis of a reception delay pattern selected according to a control signal from the apparatus control unit 13 and adds the received data to perform a reception focusing process. A sound ray signal in which the focus of an ultrasound echo subjected to phasing addition is narrowed is generated by the reception focusing process.

The signal processing unit 19 corrects the attenuation of the sound ray signal generated by the beam former 18 depending on a distance according to the depth of the reflection position of ultrasonic waves and then performs an envelope detection process. In addition, the signal processing unit 19 performs various types of necessary image processing including a gradation process to generate a B-mode image signal which is tomographic image information about the issues of the subject.

The DSC 10 of the image generation unit 3 converts the B-mode image signal generated by the signal processing unit 19 into an image signal based on a general television signal scanning system (raster conversion).

The display control unit 4 displays a B-mode image on the display unit 5 on the basis of the B-mode image signal generated by the image generation unit 3.

The display unit 5 includes a display device, such as a liquid crystal display (LCD), and displays the B-mode image under the control of the display control unit 4.

The part determination unit 11 determines an imaging part of the subject on the basis of the B-mode image signal generated by the image generation unit 3.

The probe state determination unit 12 determines whether the ultrasound probe 1 is in a contact state in which the ultrasound probe 1 comes into contact with the body surface of a subject and emits ultrasonic waves into the body of the subject or an aerial emission state in which the ultrasound probe 1 is separated from the body surface of the subject and emits ultrasonic waves to the air, on the basis of the B-mode image generated by the image generation unit 3.

The apparatus control unit 13 controls the transmission/reception control unit 8, the B-mode processing unit 9, the DSC 10, the display control unit 4, the part determination unit 11, and the probe state determination unit 12 on the basis of commands input by the operator through the operation unit 14.

The operation unit 14 is used by the operator to perform an input operation and may include, for example, a keyboard, a mouse, a trackball, and a touch panel.

The storage unit 15 stores, for example, an operation program. For example, a recording medium, such as a hard disk, a flexible disk, an MO, an MT, a RAM, a CD-ROM, a DVD-ROM, an SD card, a CF card, or a USB memory, or a server may be used as the storage unit 15.

Here, a part determination method in the part determination unit 11 will be described.

Examples of the imaging part of the subject can include the heart, the right abdomen, the left abdomen, and the urinary bladder. Of course, the part determination unit 11 may be configured so as to determine various other imaging parts.

The part determination unit 11 stores the typical pattern data of a plurality of imaging parts in advance and calculates the similarity between the B-mode image signal of the imaging part output from the DSC 10 of the image generation unit 3 and each of a plurality of pattern data items stored in advance. A known matching technique can be used to calculate the similarity. In addition to the matching technique, for example, the following method may be used to calculate the similarity: a machine learning method disclosed in Csurka et al.: Visual Categorization with Bags of Keypoints, Proc. of ECCV Workshop on Statistical Learning in Computer Vision, pp. 59-74 (2004); or a general image recognition method using deep learning disclosed in Krizhevsk et al.: ImageNet Classification with Deep Convolutional Neural Networks, Advances in Neural Information Processing Systems 25, pp. 1106-1114 (2012).

The part determination unit 11 calculates similarity scores between the B-mode image signal of the imaging part and a plurality of imaging parts, using these methods, and uses an imaging part with the highest similarity score as the determination result. For example, in a case in which the similarity score for the heart is 5, the similarity score for the right abdomen is 10, the similarity score for the left abdomen is 6, and the similarity score for the urinary bladder is 3, the determination result indicating that the captured imaging part is the right abdomen with the highest similarity score is obtained.

The determination result of the imaging part obtained by the part determination unit 11 in this way is input to the apparatus control unit 13.

Figure 4:
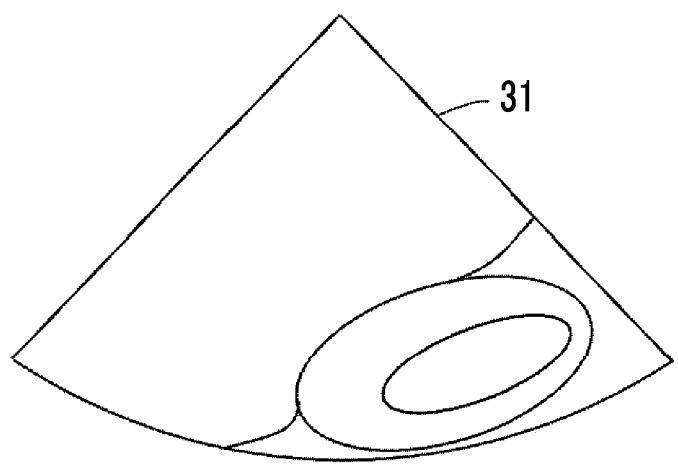
FIG. 4 is a diagram illustrating a B-mode image.

The probe state determination unit 12 determines the state of the ultrasound probe 1. In general, in a case in which the ultrasound probe 1 comes into contact with the body surface of the subject and emits ultrasonic waves into the body of the subject, a certain structure, that is, a tissue of the subject is extracted to a B-mode image 31 as illustrated in FIG. 4. In contrast, in a case in which the ultrasound probe 1 is separated from the body surface of the subject and emits ultrasonic waves to the air, no structure is extracted to the B-mode image 31.

Therefore, it is detected whether a structure is present or absent in the B-mode image 31 on the basis of a brightness distribution of the B-mode image 31. In a case in which a structure is detected in the B-mode image 31, it can be determined that the ultrasound probe 1 is in the contact state with the subject. In a case in which no structure is detected in the B-mode image 31, it can be determined that the ultrasound probe 1 is in the aerial emission state.

Figure 5:
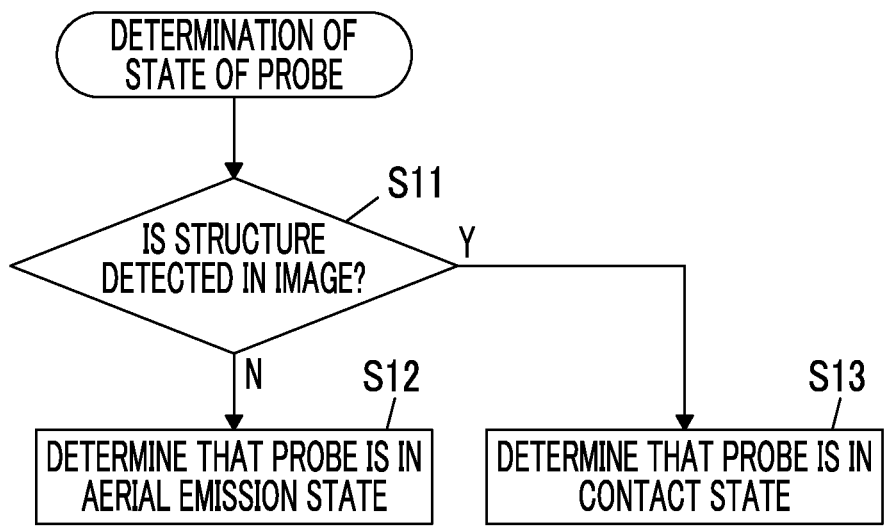
FIG. 5 is a flowchart illustrating an ultrasound probe state determination operation of a probe state determination unit.

As illustrated in the flowchart of FIG. 5, in Step S11, the probe state determination unit 12 determines whether a structure is detected in the B-mode image. In a case in which no structure is detected in the B-mode image, in Step S12, it is determined that the ultrasound probe 1 is in the aerial emission state. In a case in which a structure is detected in the B-mode image, in Step S13, it is determined that the ultrasound probe 1 is in the contact state with the subject.

Figure 6:
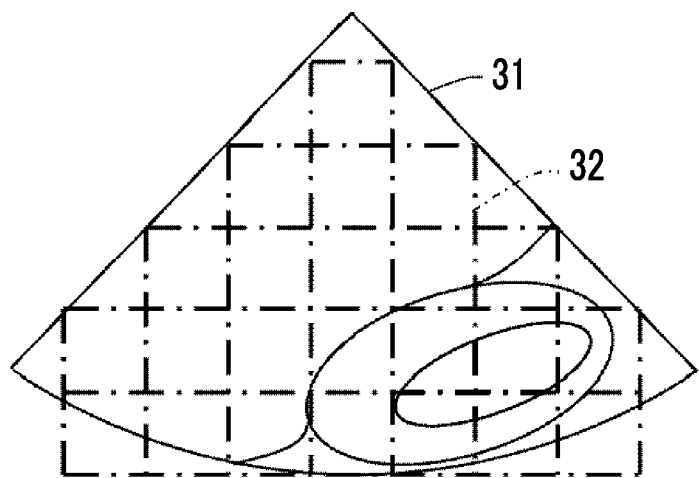
FIG. 6 is a diagram illustrating a B-mode image in which a plurality of regions of interest are set.

Specifically, as illustrated in FIG. 6, the B-mode image 31 is divided into a plurality of regions 32. The variance of the brightness of each region 32 or the difference between the maximum brightness and the minimum brightness is calculated as an index value. In a case in which the number of regions 32 with an index value that is equal to or greater than a predetermined set value is equal to or greater than a predetermined threshold value, the probe state determination unit 12 determines that the ultrasound probe 1 is in the contact state with the subject. On the other hand, in a case in which the number of regions 32 with an index value that is equal to or greater than the predetermined set value is less than the predetermined threshold value, the probe state determination unit 12 determines that the ultrasound probe 1 is in the aerial emission state.

In a case in which the ultrasound probe 1 is in the aerial emission state, it is considered that almost the same B-mode image is acquired. Therefore, the B-mode image in a case in which the ultrasound probe 1 is in the aerial emission state may be stored in advance and the probe state determination unit 12 may determine the state of the ultrasound probe 1, using a matching technique such as template matching.

As such, the state of the ultrasound probe 1 is determined on the basis of whether a structure is present or absent in the B-mode image. Therefore, the probe state determination unit 12 can determine that the ultrasound probe 1 has been changed from the aerial emission state to the contact state with the subject or that the ultrasound probe 1 has been changed from the contact state with the subject to the aerial emission state, on the basis of a change in the detection state of a structure in the B-mode image between frames.

Figure 7:
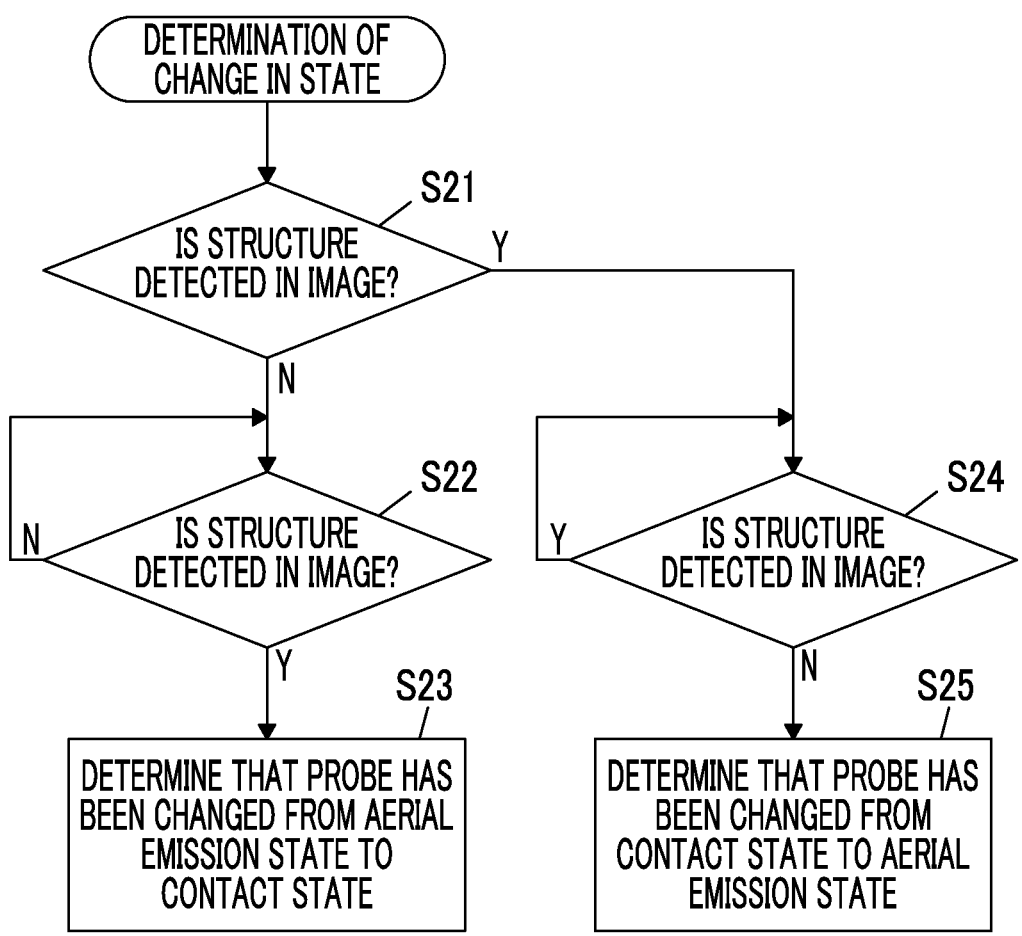
FIG. 7 is a flowchart illustrating an ultrasound probe state change determination operation of the probe state determination unit.

That is, as illustrated in the flowchart of FIG. 7, first, in Step S21, the probe state determination unit 12 determines whether a structure is detected in the B-mode image in each frame. In a case in which no structure is detected, it is determined that the ultrasound probe 1 is in the aerial emission state. Then, in Step S22, the process of determining whether a structure is detected in the B-mode image in each frame is repeatedly performed until a structure is detected in the B-mode image. Then, in a case in which a structure is detected in the B-mode image in Step S22, in Step S23, it is determined that the ultrasound probe 1 has been changed from the aerial emission state to the contact state with the subject.

In contrast, in a case in which a structure is detected in the B-mode image in Step S21, the probe state determination unit 12 determines that the ultrasound probe 1 is in the contact state with the subject. Then, in Step S24, the process of determining whether a structure is detected in the B-mode image in each frame is repeatedly performed until a structure is not detected in the B-mode image. Then, in a case in which no structure is detected in the B-mode image in Step S24, in Step S25, it is determined that the ultrasound probe 1 has been changed from the contact state with the subject to the aerial emission state.

Figure 8:
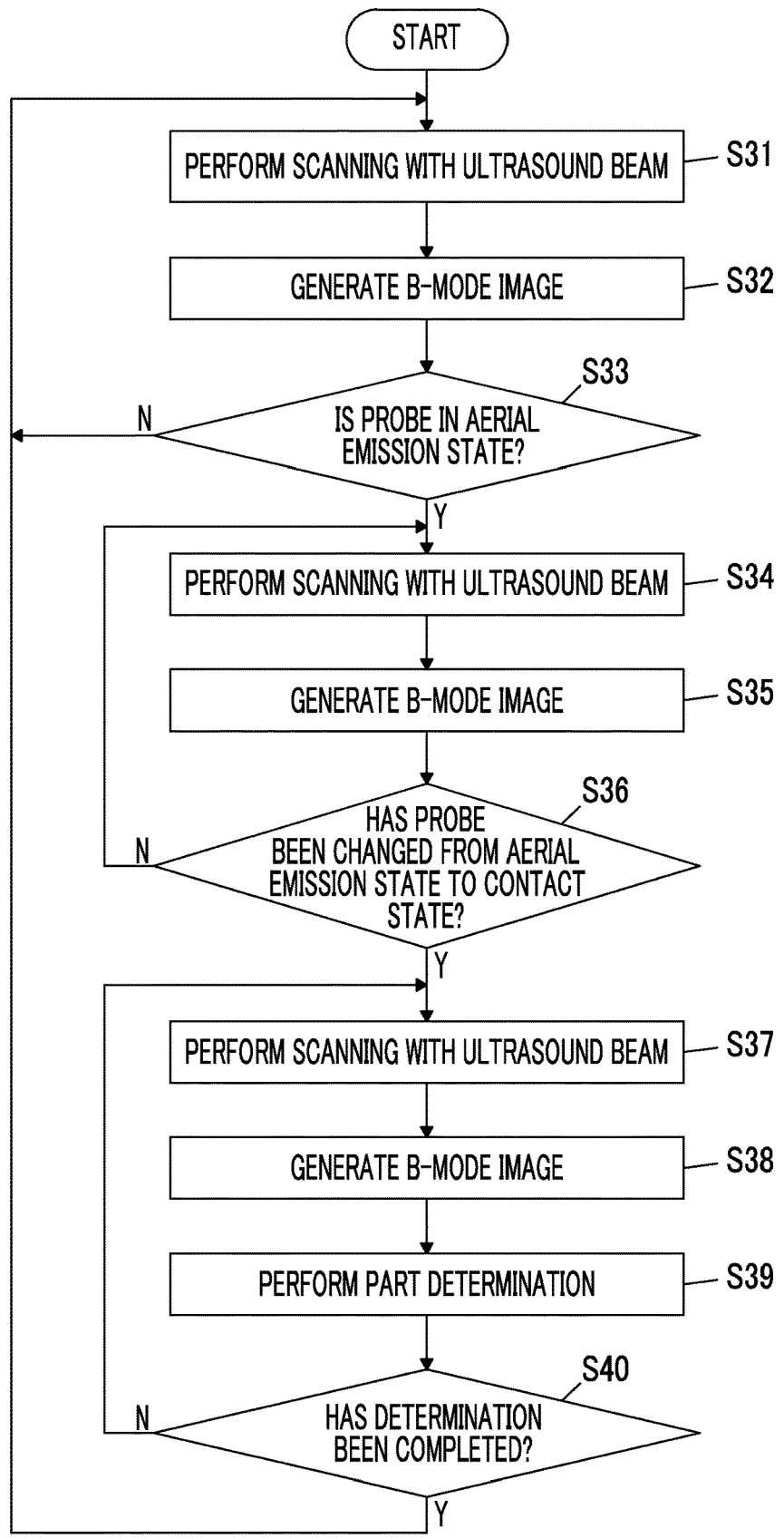
FIG. 8 is a flowchart illustrating an operation in Embodiment 1.

Next, the operation of Embodiment 1 will be described with reference to the flowchart illustrated in FIG. 8.

First, in Step S31, the transmitting/receiving unit 2 performs the transmission and reception of an ultrasound beam and scanning, using the plurality of ultrasound transducers in the array transducer 1A of the ultrasound probe 1. A received signal from each ultrasound transducer that has received ultrasound echoes from the subject is output to the receiving unit 7. The receiving unit 7 performs amplification and A/D conversion for the received signal to generate received data.

In Step S32, the received data is input to the image generation unit 3. The B-mode processing unit 9 performs the reception focusing process for the received data and the DSC 10 converts signal conversion to generate a B-mode image signal. The B-mode image signal is output from the image generation unit 3 to the display control unit 4. The B-mode image is displayed on the display unit 5.

The B-mode image signal output from the DSC 10 of the image generation unit 3 is input to the probe state determination unit 12. In Step S33, the probe state determination unit 12 determines whether the ultrasound probe 1 is in the aerial emission state. In this case, the probe state determination unit 12 determines whether the ultrasound probe 1 is in the aerial emission state or the contact state with the subject on the basis of whether a structure is detected in the B-mode image, as illustrated in the flowchart of FIG. 5.

In a case in which it is determined in Step S33 that the ultrasound probe 1 is in the aerial emission state, the process returns to Step S31 and the imaging process in Steps S31 and S32 is repeatedly performed until the ultrasound probe 1 is determined to be in the aerial emission state in Step S33. In this way, the B-mode image of the imaging part is sequentially generated and displayed on the display unit 5. Then, the imaging part is diagnosed.

Then, in a case in which it is determined in Step S33 that the ultrasound probe 1 is in the aerial emission state, the diagnosis of the imaging part ends and it is determined that the ultrasound probe 1 has been separated from the subject to be moved to the next examination part. Then, in Steps S34 and S35, the imaging process is performed again. In Step S36, the probe state determination unit 12 determines whether the ultrasound probe 1 has been changed from the aerial emission state to the contact state with the subject. In this case, the probe state determination unit 12 determines whether the ultrasound probe 1 has been changed from the aerial emission state to the contact state with the subject on the basis of a change in the detection state of a structure in the B-mode image between frames, as illustrated in the flowchart of FIG. 7.

In a case in which it is determined in Step S36 that the ultrasound probe 1 has not been changed from the aerial emission state to the contact state with the subject, the process returns to Step S34 and the imaging process in Steps S34 and S35 is repeatedly performed until the ultrasound probe 1 is determined to be changed from the aerial emission state to the contact state with the subject in Step S36.

Then, in a case in which it is determined in Step S36 that the ultrasound probe 1 has been changed from the aerial emission state to the contact state with the subject, it is determined that the ultrasound probe 1 has been moved to a new imaging part. Then, in Steps S37 and S38, the imaging process is performed again. In Step S39, the part determination unit 11 performs part determination. In a case in which the part determination is completed, the part determination unit 11 outputs the determination result for the imaging part to the apparatus control unit 13. The apparatus control unit 13 recognizes that the part determination has been completed in Step S40 in a case in which the determination result is output from the part determination unit 11.

In a case in which the completion of the part determination is checked in Step S40, the process returns to Step S31 and imaging is performed for the imaging part. Then, the imaging part is diagnosed.

As such, in a case in which it is determined that the ultrasound probe 1 is separated from the subject and is in the aerial emission state, the part determination unit 11 does not perform part determination. In a case in which it is determined that the ultrasound probe 1 has been changed from the aerial emission state to the contact state with the subject, the part determination unit 11 performs part determination. Therefore, the part determination process for the frame that does not require part determination can be omitted and it is possible to prevent an increase in the amount of calculation. Since an increase in the amount of calculation is prevented, it is possible to prevent, for example, a reduction in the frame rate. In addition, for example, since an increase in the amount of calculation is prevented, it is possible to prevent an increase in power consumption.

After the apparatus control unit 13 checks that the ultrasound probe 1 has come into contact with the subject and part determination by the part determination unit 11 has been completed, the ultrasound probe 1 is separated from the subject and the probe state determination unit 12 determines that the ultrasound probe 1 is in the aerial emission state. Then, the part determination unit 11 does not perform part determination until the ultrasound probe 1 comes into contact with the subject and the probe state determination unit 12 determines that the ultrasound probe 1 is in the contact state with the subject. Therefore, the part determination unit 11 performs part determination only in a case in which the imaging part is moved from the diagnosed imaging part to a new imaging part. As a result, it is possible to further prevent an increase in the amount of calculation while performing part determination.

Embodiment 2

Figure 9:
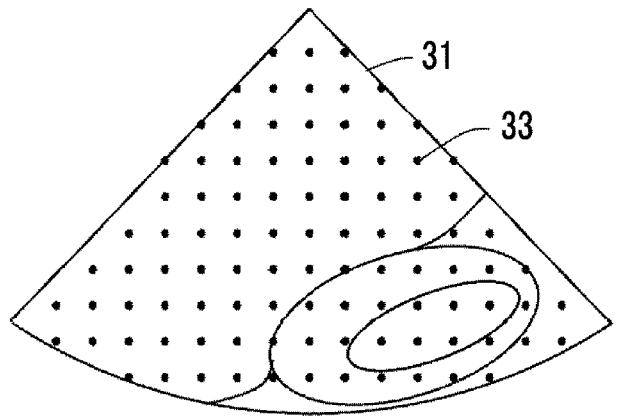
FIG. 9 is a diagram illustrating a B-mode image in which a plurality of observation points are set in Embodiment 2.

In Embodiment 1, the probe state determination unit 12 determines the state of the ultrasound probe 1 on the basis of the index value of the brightness of the plurality of regions 32 illustrated in FIG. 6. However, in addition to the analysis based on the index value of the brightness of each region 32, a plurality of observation points 33 may be set in the B-mode image 31 as illustrated in FIG. 9 and the amount of movement of each observation point 33 between frames may be detected to determine the state of the ultrasound probe 1.

The configuration of an ultrasound diagnostic apparatus according to Embodiment 2 is the same as the configuration of the ultrasound diagnostic apparatus according to Embodiment 1 illustrated in FIG. 1. However, in a case in which the number of observation points 33 of which the amount of movement between frames is equal to or less than a set value is equal to or greater than a predetermined threshold value, the probe state determination unit 12 determines that the movement of the ultrasound probe 1 is stable and determines whether the ultrasound probe 1 is in the contact state with the subject or the aerial emission state on the basis of the index value of the brightness of each region 32 illustrated in FIG. 6. In addition, the probe state determination unit 12 can determine that the ultrasound probe 1 has been changed from the aerial emission state to the contact state with the subject or that the ultrasound probe 1 has been changed from the contact state with the subject to the aerial emission state on the basis of a change in the detection state of a structure in the B-mode image between frames.

Figure 10:
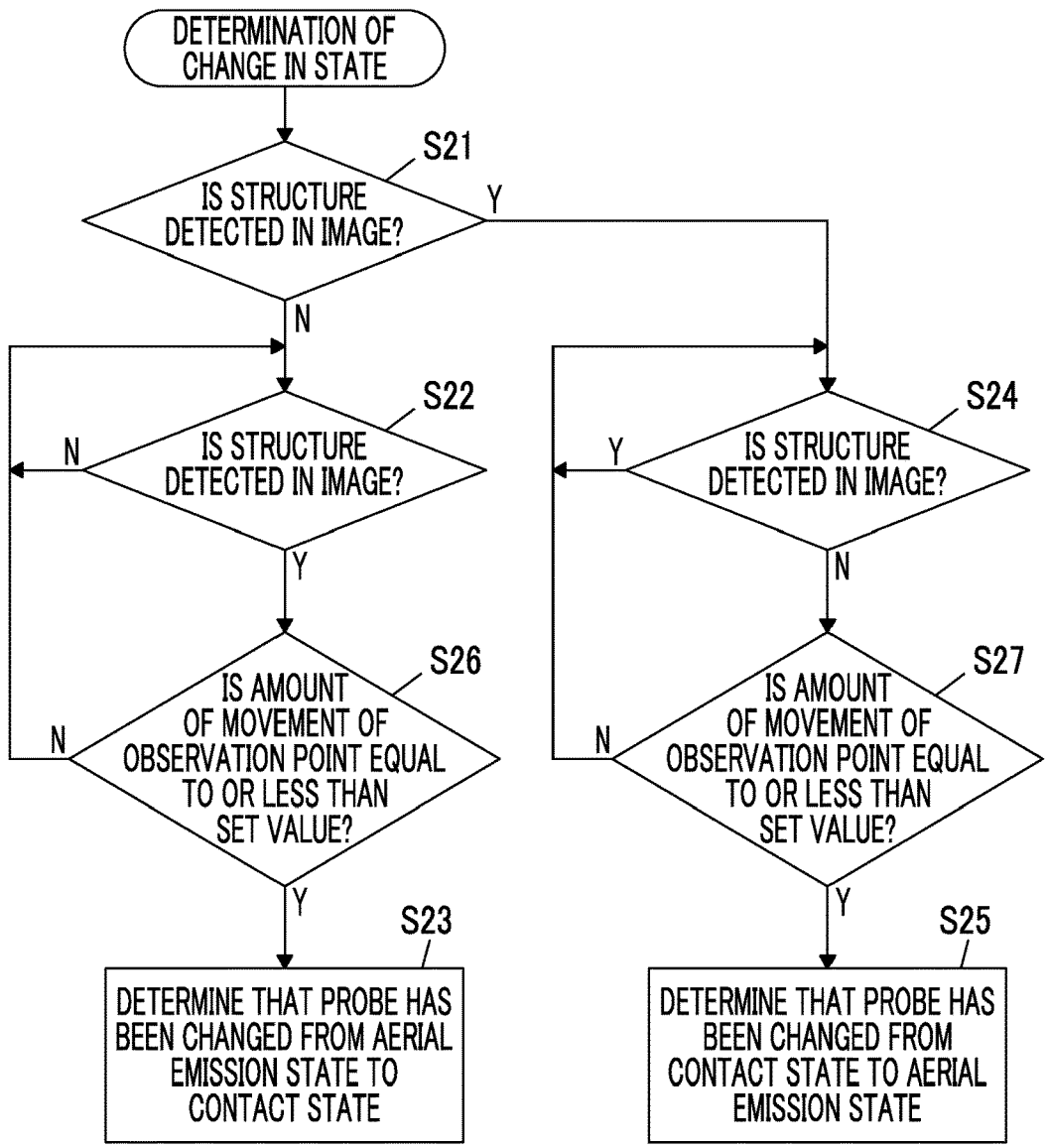
FIG. 10 is a flowchart illustrating an ultrasound probe state change determination operation in Embodiment 2.

That is, as illustrated in the flowchart of FIG. 10, similarly to Embodiment 1, in a case in which a structure is not detected in the B-mode image in Step S21, in Step S22, the probe determination unit 12 repeatedly performs the process of determining whether a structure is detected in the B-mode image in each frame until a structure is detected. In a case in which a structure is detected in the B-mode image in Step S22, in Step S26, the probe determination unit 12 checks whether the amount of movement of the plurality of observation points 33 between frames is equal to or less than the set value. In a case in which the amount of movement of the plurality of observation points 33 between frames is greater than the set value, the probe determination unit 12 determines that the movement of the ultrasound probe 1 is not stable and returns to Step S22. Then, the probe determination unit 12 repeatedly performs the process of determining whether a structure is detected and the process of detecting the amount of movement between frames until the amount of movement of the plurality of observation points 33 between frames is less than the set value.

Then, in a case in which it is checked in Step S26 that the amount of movement of the plurality of observation points 33 between frames is less than the set value, in Step S23, the probe determination unit 12 determines that the movement of the ultrasound probe 1 is stable and determines that the ultrasound probe 1 has been changed from the aerial emission state to the contact state with the subject.

On the other hand, in a case in which a structure is detected in the B-mode image in Step S21, in Step S24, the probe determination unit 12 repeatedly performs the process of determining whether a structure is detected in the B-mode image in each frame until a structure is not detected. In a case in which no structure is detected in the B-mode image in Step S24, in Step S27, the probe determination unit 12 checks whether the amount of movement of the plurality of observation points 33 between frames is equal to or less than the set value. In a case in which the amount of movement of the plurality of observation points 33 between frames is greater than the set value, the probe determination unit 12 determines that the movement of the ultrasound probe 1 is not stable and returns to Step S24. The probe determination unit 12 repeatedly performs the process of determining whether a structure is detected and the process of detecting the amount of movement between frames until the amount of movement of the plurality of observation points 33 between frames is less than the set value.

Then, in a case in which it is checked in Step S27 that the amount of movement of the plurality of observation points 33 between frames is less than the set value, in Step S25, the probe determination unit 12 determines that the movement of the ultrasound probe 1 is stable and determines that the ultrasound probe 1 has been changed from the contact state with the subject to the aerial emission state.

As such, the ultrasound diagnostic apparatus according to Embodiment 2 determines a change in the state of the ultrasound probe 1, considering the amount of movement of the plurality of observation point 33 between frames. Therefore, it is possible to perform part determination after the movement of the ultrasound probe 1 is stabilized. In a situation in which the movement of the ultrasound probe 1 is unstable and a determination error occurs, the part determination process is prohibited. Therefore, it is possible to further prevent an increase in the amount of calculation and to improve the accuracy of part determination.

After the movement of the ultrasound probe 1 is stabilized, it is determined in Step S25 that the ultrasound probe 1 has been changed from the contact state with the subject to the aerial emission state on the basis of the amount of movement of the plurality of observation points 33 between frames. Therefore, in a case in which the ultrasound probe 1 is instantaneously separated from the body surface of the subject by an operation mistake while an examination part is diagnosed, it is possible to prevent the ultrasound probe 1 from being immediately determined to be in the aerial emission state and to prevent part determination from being repeatedly performed for the same examination part.

EXPLANATION OF REFERENCES

1: ultrasound probe
1A: array transducer
2: transmitting/receiving unit
3: image generation unit
4: display control unit
5: display unit
6: transmitting unit
7: receiving unit
8: transmission/reception control unit
9: B-mode processing unit
10: DSC
11: part determination unit
12: probe state determination unit
13: apparatus control unit
14: operation unit
15: storage unit
16: amplification unit
17: A/D converter 18: beam former
19: signal processing unit
31: B-mode image
32: region
33: observation point

What is claimed is:

1. An ultrasound diagnostic apparatus comprising:
an ultrasound probe;
a processor configured to:
   transmit and receive an ultrasound beam to and from a subject using the ultrasound probe and convert a received signal output from the ultrasound probe into an image to generate an ultrasound image of the subject for each frame;
   determine whether the ultrasound probe is in an aerial emission state or a contact state with the subject; and
   perform a determination of an imaging part of the subject using the ultrasound image when it is determined that the ultrasound probe has been changed from the aerial emission state to the contact state with the subject and not to perform the determination of the imaging part of the subject using the ultrasound image when it is determined that the ultrasound probe is in the aerial emission state,
wherein, after it is recognized that the part determination has been completed, the processor does not perform the part determination until the ultrasound probe is determined to be changed from the aerial emission state to the contact state with the subject.

2. The ultrasound diagnostic apparatus according to claim 1,
wherein the processor detects whether a structure is present or absent in an image on the basis of a brightness distribution of the ultrasound image,
when no structure is detected in the image, the processor determines that the ultrasound probe is in the aerial emission state, and
when a structure is detected in the image, the processor determines that the ultrasound probe is in the contact state with the subject.

3. The ultrasound diagnostic apparatus according to claim 2,
wherein the processor further detects an amount of movement of an observation point set in the ultrasound image between frames,
when a state in which no structure is detected in the image changes to a state in which a structure is detected in the image and the amount of movement of the observation point detected is equal to or less than a predetermined amount of movement, the processor determines that the ultrasound probe has been changed from the aerial emission state to the contact state with the subject, and
when the state in which a structure is detected in the image changes to the state in which no structure is detected in the image and the amount of movement of the observation point detected is equal to or less than the predetermined amount of movement, the processor determines that the ultrasound probe has been changed from the contact state with the subject to the aerial emission state.

4. The ultrasound diagnostic apparatus according to claim 3,
wherein the processor calculates similarity between the ultrasound image and each imaging part and outputs a determination result on the basis of the similarity, and recognizes that the part determination has been completed by the determination result being output.

5. The ultrasound diagnostic apparatus according to claim 2,
wherein the processor calculates similarity between the ultrasound image and each imaging part and outputs a determination result on the basis of the similarity, and recognizes that the part determination has been completed with the determination result being output.

6. The ultrasound diagnostic apparatus according to claim 1,
wherein the processor calculates similarity between the ultrasound image and each imaging part and outputs a determination result on the basis of the similarity, and recognizes that the part determination has been completed by the determination result being output.

7. A method for controlling an ultrasound diagnostic apparatus, the method comprising:
a step of transmitting and receiving an ultrasound beam to and from a subject using an ultrasound probe and converting a received signal output from the ultrasound probe into an image to generate an ultrasound image of the subject for each frame;
a step of determining whether the ultrasound probe is in an aerial emission state or a contact state with the subject; and
a step of determining an imaging part of the subject on the basis of the ultrasound image when it is determined that the ultrasound probe has been changed from the aerial emission state to the contact state with the subject and of not determining the imaging part of the subject on the basis of the ultrasound image when it is determined that the ultrasound probe is in the aerial emission state,
wherein, after it is recognized that determination of the imaging part in the step of determining the imaging part has been completed, a subsequent determination of the imaging part is not performed until the ultrasound probe is determined to be changed from the aerial emission state to the contact state with the subject.

8. The method for controlling an ultrasound diagnostic apparatus according to claim 7,
wherein the step of determining a state of the ultrasound probe comprises:
detecting whether a structure is present or absent in an image on the basis of a brightness distribution of the ultrasound image;
when no structure is detected in the image, determining that the ultrasound probe is in the aerial emission state; and
when a structure is detected in the image, determining that the ultrasound probe is in the contact state with the subject.

9. The method for controlling an ultrasound diagnostic apparatus according to claim 8,
wherein the step of determining a state of the ultrasound probe further comprises:
detecting an amount of movement of an observation point set in the ultrasound image between frames;
when a state in which no structure is detected in the image changes to a state in which a structure is detected in the image and the amount of movement of the observation point detected is equal to or less than a predetermined amount of movement, determining that the ultrasound probe has been changed from the aerial emission state to the contact state with the subject, and
when the state in which a structure is detected in the image changes to the state in which no structure is detected in the image and the amount of movement of the observation point detected is equal to or less than the predetermined amount of movement, determining that the ultrasound probe has been changed from the contact state with the subject to the aerial emission state.

10. The method for controlling an ultrasound diagnostic apparatus according to claim 9,
wherein the step of determining the imaging part comprises:
calculating similarity between the ultrasound image and each imaging part and outputting a determination result on the basis of the similarity, and
recognizing that the determination of the imaging part has been completed with the determination result being output.

11. The method for controlling an ultrasound diagnostic apparatus according to claim 8,
wherein the step of determining the imaging part comprises:
calculating similarity between the ultrasound image and each imaging part and outputting a determination result on the basis of the similarity, and
recognizing that the determination of the imaging part has been completed with the determination result being output.

12. The method for controlling an ultrasound diagnostic apparatus according to claim 7,
wherein the step of determining the imaging part comprises:
calculating similarity between the ultrasound image and each imaging part and outputting a determination result on the basis of the similarity, and
recognizing that the determination of the imaging part has been completed with the determination result being output.

* * * * *